United States Patent
Grocott

(10) Patent No.: US 12,420,928 B2
(45) Date of Patent: Sep. 23, 2025

(54) AIRCRAFT GALLEY PATHOGEN TEST KIT

(71) Applicant: B/E Aerospace, Inc., Winston Salem, NC (US)

(72) Inventor: Edward Grocott, Winston-Salem, NC (US)

(73) Assignee: B/E Aerospace, Inc., Winston Salem, NC (US)

(*) Notice: Subject to any disclaimer, the term of this patent is extended or adjusted under 35 U.S.C. 154(b) by 495 days.

(21) Appl. No.: 17/368,422

(22) Filed: Jul. 6, 2021

(65) Prior Publication Data

US 2022/0001988 A1 Jan. 6, 2022

Related U.S. Application Data

(60) Provisional application No. 63/048,339, filed on Jul. 6, 2020.

(51) Int. Cl.
| | |
|---|---|
| *B64D 11/04* | (2006.01) |
| *A61L 2/10* | (2006.01) |
| *A61L 2/26* | (2006.01) |
| *B64D 47/02* | (2006.01) |

(52) U.S. Cl.
CPC ............... *B64D 11/04* (2013.01); *A61L 2/10* (2013.01); *A61L 2/26* (2013.01); *B64D 47/02* (2013.01); *A61L 2202/11* (2013.01); *A61L 2202/24* (2013.01)

(58) Field of Classification Search
CPC ........... B64D 11/04; B64D 47/02; A61L 2/10; A61L 2/26; A61L 2202/11; A61L 2202/24
See application file for complete search history.

(56) References Cited

U.S. PATENT DOCUMENTS

| | | | |
|---|---|---|---|
| 9,439,023 B2 * | 9/2016 | Bialas | A61B 50/13 |
| 9,968,697 B1 | 5/2018 | Philipps | |
| 10,253,346 B2 * | 4/2019 | Auner | G01N 21/65 |
| 10,442,535 B2 * | 10/2019 | McKee | B64D 11/003 |
| 10,883,261 B2 * | 1/2021 | Goeschel | B64C 1/1453 |
| 10,923,216 B1 * | 2/2021 | White | H04L 9/3231 |
| 11,273,915 B2 * | 3/2022 | Rowe | A47B 77/04 |
| 2008/0188719 A1 | 8/2008 | Kemlen | |
| 2009/0314889 A1 * | 12/2009 | Baatz | B64D 11/0007 244/118.5 |
| 2016/0338488 A1 * | 11/2016 | Garcia | A47B 31/06 |
| 2017/0107659 A1 | 4/2017 | Hills | |
| 2018/0318457 A1 * | 11/2018 | Lucio | A61L 2/0047 |
| 2019/0292765 A1 | 9/2019 | Goeschel et al. | |

OTHER PUBLICATIONS

Extended European Search Report issued in corresponding European patent application No. 21184127.5, issued Dec. 7, 2021. (4 pages).

* cited by examiner

*Primary Examiner* — Joshua D Huson
*Assistant Examiner* — Vicente Rodriguez
(74) *Attorney, Agent, or Firm* — SNELL & WILMER L.L.P.

(57) ABSTRACT

A galley monument for a cabin area of an aircraft including a first monument stack, a second monument stack adjacent to the first monument stack, a tray within the second monument stack to secure a rapid pathogen tester, a slidably moveable support located below the tray to secure a plurality of tools to use along with the rapid pathogen tester, and at least one light within the tray to irradiate the tools placed within the support.

21 Claims, 2 Drawing Sheets

AIRCRAFT GALLEY PATHOGEN TEST KIT

PRIORITY

The present application claims priority to U.S. provisional application No. 63/048,339, filed on Jul. 6, 2020, the contents of which are here entirely incorporated by reference.

BACKGROUND

Technological Field

The present disclosure relates generally to galley monuments, and more particularly to galley monuments capable of securing pathogen test kits.

Description of Related Art

With the COVID-19 pandemic illuminating the need for passengers and airlines to feel secure that each and every of their passengers is able to fly as planned, and able to contact trace it became evident that current testing models and methods are not enough to supply to passengers that type of assuredness and security. While conventional testing methods required passengers to take test at most three days before flying, nothing assured airlines or fellow passengers that no one became infected in the three subsequent days. Thus on board testing machines were created. However, galleys and aircraft had to be retrofit to be able to secure these new machines that had never previously been on aircraft within the galleys. There also had to be a method of cleaning these machines since they are constantly coming into contact with potentially ill or infected passengers. The present disclosure provides a solution for this need.

SUMMARY OF THE INVENTION

A galley monument for a cabin area of an aircraft is disclosed. The monument includes including a first monument stack, a second monument stack adjacent to the first monument stack, a tray within the second monument stack to secure a rapid pathogen tester, a slidably moveable support located below the tray to secure a plurality of tools to use along with the rapid pathogen tester, and at least one light within the tray to irradiate the tools placed within the support. It is further considered that a tray in a stack adjacent to the second monument stack to secure the tester when in use.

It is further considered that the light can be a UV light. The light can be attached to an underside of the tray. The light can protrude out of the underside of the tray. The light can be positioned such that it irradiates at least three sides of the support.

It is further considered that the tray can include an indentation for bordering the pathogen tester, which can include a rectangular footprint. An elevation can surround the indentation from at least three sides or from four sides.

It is further considered that the support can be a drawer held up by rails. The tray can include at least one aperture for threading wiring to power the light and the tray can be attached to the stack.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein.

DETAILED DESCRIPTION

Figure 1:
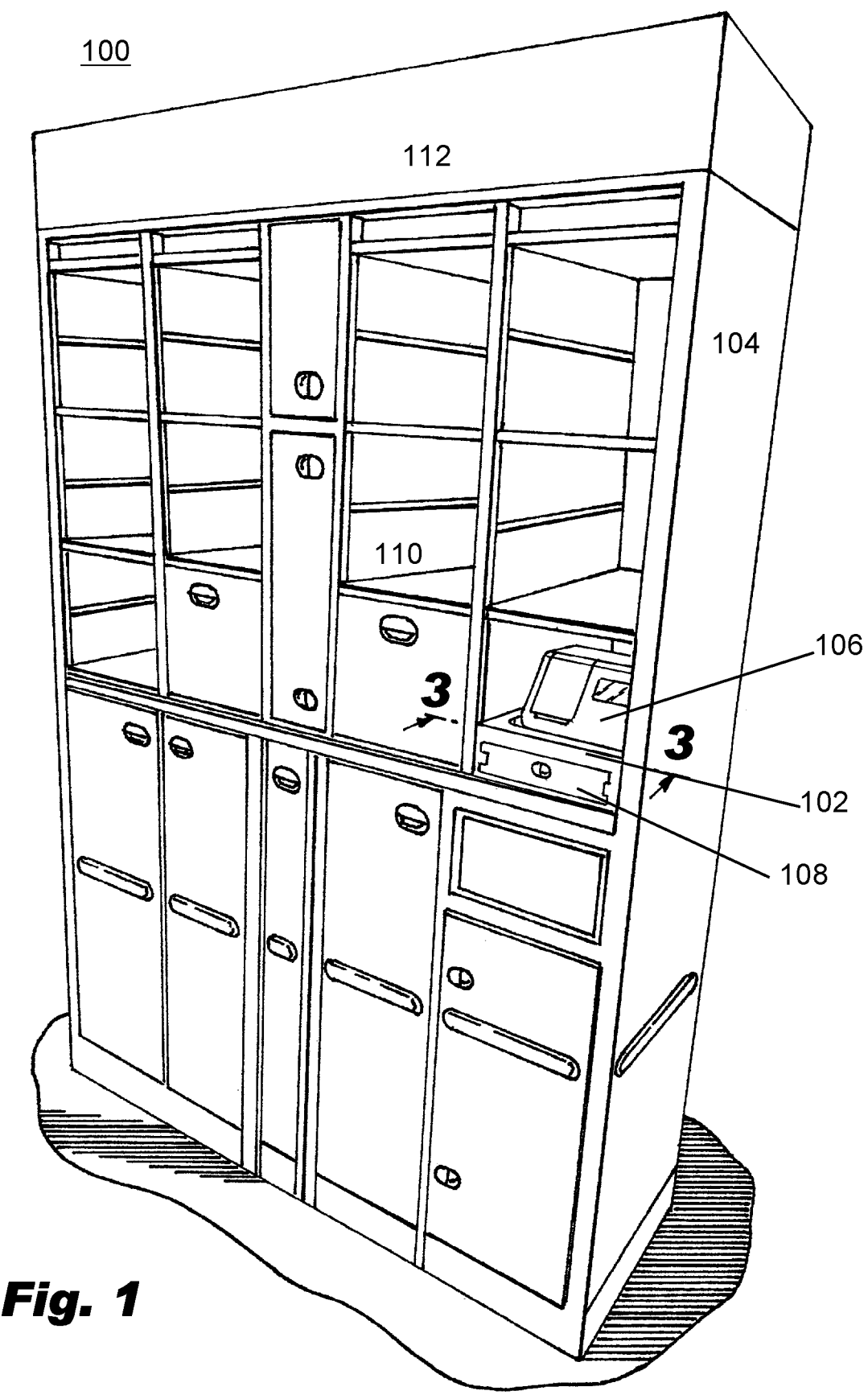
FIG. 1 is a perspective view of an exemplary embodiment of a galley monument for a cabin area of an aircraft.
Figure 2:
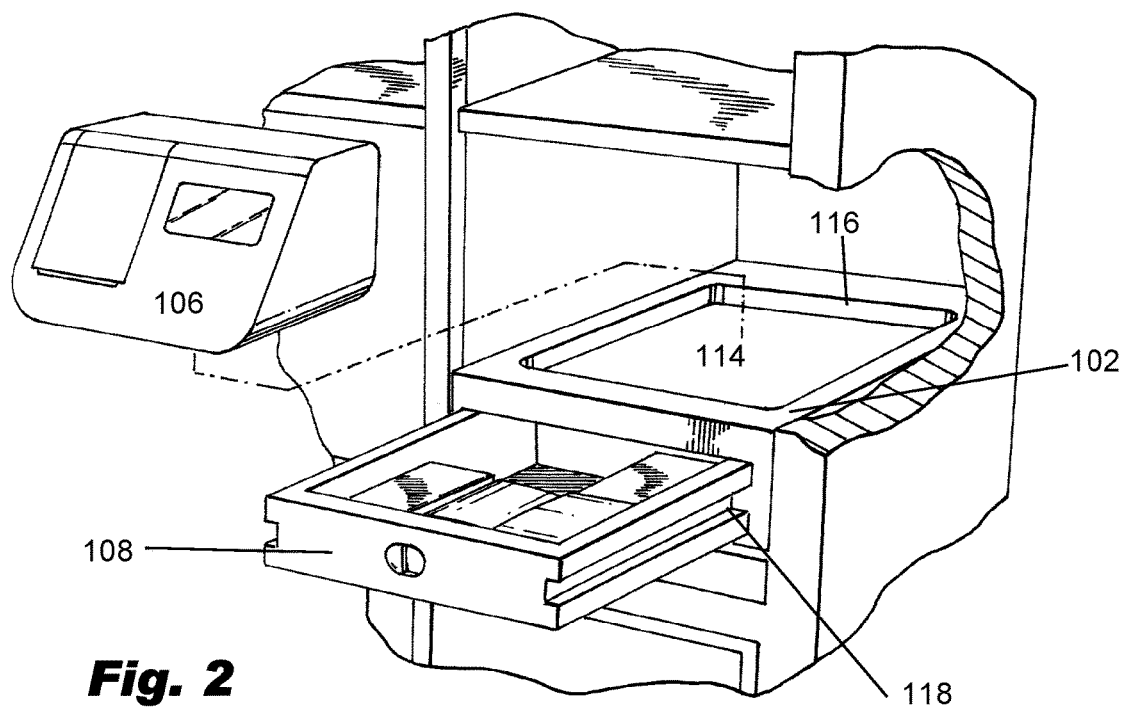
FIG. 2 is an exploded view of a tray and the support of FIG. 1.
Figure 3:
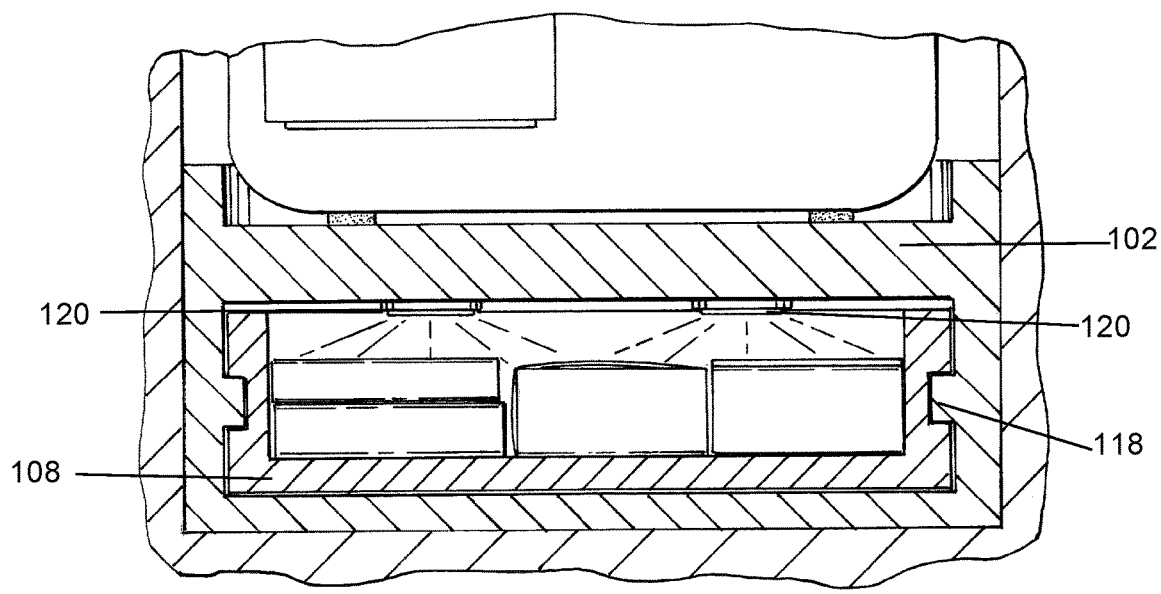
FIG. 3 is cross sectional view showing a shining light and contents of the support of FIG. 2.

Reference will now be made to the drawings wherein like reference numerals identify similar structural features or aspects of the subject disclosure. For purposes of explanation and illustration, and not limitation, a partial view of an exemplary embodiment of a galley monument and tester storage in accordance with the disclosure is shown in FIG. 1. Other embodiments of the galley monument in accordance with the disclosure, or aspects thereof, are provided in FIGS. 2 and 3, as will be described. The galley monument described herein can be used for storage of an essential, tester on board the aircraft, and sanitation of the tools associated with said tester. Referring now to FIGS. 1-3, FIG. 1 shows a galley monument 100 that is placed within a main cabin of an aircraft. The monument 100 is shown with a plurality of stacks, where each stack has numerous compartments for storage of food preparation and items for passenger comfort. A tray 102 is shown within one of the stacks 104 which is used to secure a rapid pathogen tester 106 during flight. The rapid pathogen tester 106 may be configured to test for COVID-19. The rapid pathogen tester 106 may be configured to provide results of a swab taken on board an aircraft within 60 minutes. The rapid pathogen tester 106 may be configured to provide results of a swab taken on board an aircraft within 5 minutes. The rapid pathogen tester 106 may also be called a tester 106. The tray 102 is used when the tester 106 is not being used. Underneath the tray 102, a sliding support 108 is positioned to store whatever tools and items are necessary, such as swabs, and anything else that might come in contact with a potentially contagious passenger. A tray 110 in an adjacent stack 112 is utilized when the tester needs to be used. The tray 110 is higher than the first tray 102, so that it is more accessible to flight attendants.

FIG. 2 shows a close-up of the tray 102. The tray 102 includes an indentation 114 for defining where the tester is placed. The tester 106 is secured within the rectangular indentation 114. An elevation 116 surrounds the indentation 114 from all four sides. The elevation 116 is necessary that the tester 106 stays in place during turbulence. The interior of the elevation 116 may be shaped complementary to the outer shape of the tester 106. The support 108, which slides in and out is held up by rails 118. The tray 102 can include at least one aperture for threading wiring. The tester 106 can be prevented from falling out the tray 102 by using turn-buttons, or similar restraining methods. The tester 106 can be secured to the tray 102 by an adhesive, or similar restraining methods.

FIG. 3 shows the inside of the support 108. Two cleansing lights 120 are attached on the underside of the tray 102. The lights 120 are meant to irradiate the tools and items within the support 108, and walls of the support 108. The lights 120 can be UV lights or any other type of light capable of disinfecting surfaces. The lights 120 can protrude out of the underside of the tray 102 instead of being flush so that even the underside of the tray 102 is disinfected by the lights 120.

The methods and systems of the present disclosure, as described above and shown in the drawings, provide for a galley monuments capable of securing and disinfecting a rapid tester machine that is capable of testing passengers for pathogens, bacteria, and viruses. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. A galley monument for a cabin area of an aircraft comprising:
    a first monument stack including an elevated tray disposed at a first elevation;
    a second monument stack adjacent to the first monument stack; and a system within the second monument stack, the system including:
    a rapid pathogen tester;
    a storage tray disposed at a second elevation and configured to secure the rapid pathogen tester during turbulence, the second elevation being less than the first elevation;
    a plurality of tools;
    a slideable support located below the storage tray configured to secure the plurality of tools to use along with the rapid pathogen tester; and
    at least one light within the storage tray to irradiate the plurality of tools placed within the support.

2. The monument of claim 1, wherein the light is a UV light.

3. The monument of claim 1, wherein the light is attached to an underside of the storage tray.

4. The monument of claim 1, wherein the light protrudes out of the underside of the storage tray such that the light is configured to disinfect the underside of the storage tray.

5. The monument of claim 1, wherein the storage tray includes an indentation for bordering the pathogen tester.

6. The monument of claim 5, further comprising:
    an adhesive configured to secure the rapid pathogen tester to the storage tray; and
    an elevation surrounding the indentation, the elevation having an interior shape complementary to an outer shape of the rapid pathogen tester.

7. The monument of claim 6, wherein the elevation surrounds the indentation from at least three sides.

8. The monument of claim 6, wherein the elevation surrounds the indentation from four sides.

9. The monument of claim 1, wherein the light is placed such that it irradiates at least three sides of the support.

10. The monument of claim 1, further comprising rails to engage the support.

11. The monument of claim 1, wherein the support is a drawer.

12. The monument of claim 1, wherein the storage tray and the elevated tray each includes at least one aperture for threading wiring to power the light.

13. The monument of claim 1, wherein the rapid pathogen tester includes a rectangular footprint.

14. The monument of claim 1, wherein the storage tray is attached to the stack.

15. The monument of claim 1, wherein the rapid pathogen tester is configured to test for COVID-19.

16. The monument of claim 1, wherein the elevated tray is configured to secure the rapid pathogen tester when in use.

17. A galley monument for a cabin area of an aircraft comprising:
    a first monument stack;
    a second monument stack adjacent to the first monument stack; and a system within the second monument stack, the system including:
    a rapid pathogen tester;
    a tray having an indentation surrounded by an elevation having an interior shape complementary to an outer shape of the rapid pathogen tester, the indentation configured to secure the rapid pathogen tester during turbulence;
    a plurality of tools;
    a slideable support located below the tray configured to secure the plurality of tools to use along with the rapid pathogen tester; and
    at least one light within the tray to irradiate the plurality of tools placed within the support.

18. The monument of claim 17, further comprising at least one of an adhesive or a turnbutton configured to secure the rapid pathogen tester to the tray.

19. The monument of claim 17, wherein the light is a UV light.

20. The monument of claim 19, wherein the UV light is placed such that it irradiates at least three sides of the support.

21. The monument of claim 17, wherein the support is a drawer.

* * * * *